United States Patent [19]

Tsuji

[11] Patent Number: 5,068,719
[45] Date of Patent: * Nov. 26, 1991

[54] ENDOSCOPE PHOTOMETRIC APPARATUS

[75] Inventor: Kiyoshi Tsuji, Musashino, Japan

[73] Assignee: Olympus Optical Co., Ltd., Tokyo, Japan

[*] Notice: The portion of the term of this patent subsequent to Sep. 17, 2008 has been disclaimed.

[21] Appl. No.: 476,062

[22] Filed: Feb. 1, 1990

[30] Foreign Application Priority Data

Jun. 7, 1989 [JP] Japan ................................. 1-144834
Sep. 22, 1989 [JP] Japan ................................. 1-247493

[51] Int. Cl.$^5$ .............................................. H04N 7/18
[52] U.S. Cl. .................................... 358/98; 358/220; 128/4; 128/6
[58] Field of Search ...................... 358/98, 220; 128/4, 128/6

[56] References Cited

U.S. PATENT DOCUMENTS

| | | | |
|---|---|---|---|
| 4,407,272 | 10/1983 | Yamaguchi | 128/6 |
| 4,561,429 | 12/1985 | Sato | 128/6 |
| 4,667,225 | 5/1987 | Kanda | 358/36 |
| 4,780,762 | 10/1988 | Nagasaki | 358/98 X |
| 4,834,070 | 5/1989 | Saitou | 358/98 |
| 4,866,516 | 9/1989 | Hibino | 358/98 |
| 4,872,029 | 10/1989 | Kato | 358/98 |
| 4,873,572 | 10/1989 | Miyazaki | 358/98 |
| 4,901,142 | 2/1990 | Ikuno | 358/98 |

FOREIGN PATENT DOCUMENTS

| | | |
|---|---|---|
| 56-107674 | 8/1981 | Japan . |
| 57-17291 | 1/1982 | Japan . |
| 61-34793 | 10/1986 | Japan . |
| 62-110369 | 5/1987 | Japan . |
| 62-272768 | 11/1987 | Japan . |
| 1-200783 | 8/1989 | Japan . |
| 1-218194 | 8/1989 | Japan . |

Primary Examiner—James J. Groody
Assistant Examiner—Sherrie Hsia
Attorney, Agent, or Firm—Armstrong, Nikaido, Marmelstein, Kubovcik & Murray

[57] ABSTRACT

An endoscope photometric apparatus includes a photometric apparatus for detecting the brightness of an image based on an image signal from an endoscope imaging apparatus. An extracting apparatus extracts, from the image signal from the imaging apparatus, a bright part in which the brightness level from the peripheral of the image is above a predetermined value and the spatial size of the bright part is below a predetermined value. A limiting device limits the input image signal into the photometric apparatus of the part, corresponding to the bright part, in the image signal by using the output of the extracting apparatus in order to reduce the influence of the bright part on the brightness of the entire image.

15 Claims, 9 Drawing Sheets

ENDOSCOPE PHOTOMETRIC APPARATUS

BACKGROUND OF THE INVENTION

1. Field of the Invention

This invention relates to a photometric apparatus for detecting the brightness of an image based on an image signal from an endoscope imaging apparatus.

2. Related Art Statement

Recently, a video camera apparatus such as an electronic endoscope apparatus obtains an image signal using as an imaging means a solid state imaging device such as a CCD (charge coupled device).

FIG. 15 is a formation diagram of an example of the above mentioned electronic endoscope apparatus. An electronic endoscope apparatus 1 comprises an electronic scope 2 formed to be elongate so as to be inserted, for example, into a body cavity. A body unit 3 is connected to a universal cord (not illustrated) of the above mentioned scope 2. A monitor 4 displays an object to be photographed such as a body cavity interior part 5 from an output signal of the body unit 3.

A light guide 6, transmitting an illuminating light, is inserted through the insertable part of the above mentioned electronic scope 2 so that the illuminating light fed to the entrance end from the body unit 3 may be transmitted to the exit end and may be radiated toward the body cavity interior part 5. The light reflected from the body cavity interior part 5 is condensed by an objective lens 7, enters an imaging device 8 and is photoelectrically converted to be an image signal which is input to the body unit 3.

The above mentioned electronic scope 2 has a channel 9 through which a treating instrument 10 can be inserted into the body cavity. There are many treating instruments 10 which may be used such as a treating instrument having a function of injecting a coloring agent or image forming agent and a treating instrument having a function of taking out a part of tissues within a body cavity. Most of the treating instruments are made of white Teflon and metal.

The above mentioned body unit 3 comprises a light source part 20 illuminating an object to be imaged and an image signal processing part 30 outputting a video signal to a monitor 4. The above mentioned light source part 20 comprises a lamp 21, an iris 22 adjusting the light amount of the illuminating light of the lamp 21, an iris controlling circuit 23 generating a control signal for variably controlling the opening rate of the iris 22 and a photometric circuit 24 measuring the illuminating intensity of the light entering the imaging device 8 from the image signal and generating a signal to the iris controlling circuit 23. The above mentioned image signal processing part 30 comprises an AGC circuit 31 amplifying the image signal to a proper level, a photometric circuit 33 measuring the illuminating intensity of the illuminating light entering the imaging device 8 from the image signal and generating a signal to the AGC circuit 31 and a signal processing circuit 32 for variously processing the signal and outputting it to the monitor 4.

The above mentioned photometric circuits 24 and 33 are largely divided into an average photometric circuit and a peak photometric circuit. The above mentioned average photometric circuit is a circuit detecting the average value of the image signal levels of the entire picture and generating a signal so that, in case the average value of the image signal levels is high, the opening of the above mentioned iris 22 may be narrowed and the light amount of the illuminating light radiated toward the body cavity interior part 5 may be reduced. The above mentioned peak photometric circuit is a circuit detecting the maximum value of the image signal levels and generating a signal so that, in case the maximum value of the image signal levels is high, the opening of the above mentioned iris 22 may be narrowed and the light amount of the illuminating light radiated toward the body cavity interior part 5 may be reduced.

The above mentioned AGC circuit 31 is a circuit amplifying to a proper level the low image signal level which can not be compensated even by making the light amount of the illuminating light a maximum by expanding the opening of the above mentioned iris 22 to a maximum.

When the above mentioned electronic scope 2 is inserted into a body cavity and the treating instrument 10 is inserted through the channel 9, an image such as is shown in an example in FIG. 16 will be able to be observed in the monitor 4. FIG. 17 illustrates image signal levels by a time series of horizontal positions by noting a horizontal scanning line A—A' of the image shown in FIG. 16. The treating instrument 10 projects in a position nearer to the imaging device 8 than to the body cavity interior part 5. As white Teflon or the like is used, the illuminating light will be reflected at a high efficiency. As illustrated in FIG. 17, the image signal level $V_s$ will become much higher than the average value $V_a$ of the image signal levels of the body cavity part 5. Therefore, in the photometric circuits 24 and 33, the average value will become high in the average photometric circuit and the maximum value will become high in the peak photometric circuit. Therefore, the signals generated by the photometric circuits 24 and 33 will not be of proper values, the light amount for the body cavity interior part 5 will be reduced and the amplifying degree of the AGC circuit 31 will also be reduced. Therefore, the image in the monitor 4 will become dark as a whole.

A prior art of reducing the influence on the object imaging of the level variation of the image signal in a specific part in an imaged picture is disclosed, for example, in a Japanese patent application laid open No. 110369/1987.

However, the above mentioned prior art example is effective only to object higher in the luminance in a peripheral part of the imaged picture than in the central part of the picture but is not effective for an object of high luminance over the range from a peripheral part to the central part of the picture by the treating instrument or the like, for example, in an electronic endoscope apparatus.

OBJECT AND SUMMARY OF THE INVENTION

An object of the present invention is to provide an endoscope photometric apparatus wherein an object of a luminance higher than the average luminance of the imaged picture will not influence the entire imaged picture.

An endoscope photometric apparatus of the present invention comprises a photometric device for detecting the brightness of an image based on an image signal from an endoscope imaging apparatus, an extracting device for extracting from the image signal, from the above mentioned imaging apparatus, a bright part in which the difference in the brightness level at the periphery of the image is above a predetermined value and the spatial size is below a predetermined value and a limiting device for limiting the input into the above mentioned photometric device, of the part corresponding to the above mentioned bright part in the above mentioned image signal, by using the output of the above mentioned extracting device in order to reduce the influence of the above mentioned bright part on the brightness of the entire image.

The other features and advantages of the present invention will become apparent with the following explanation.

BRIEF DESCRIPTION OF THE DRAWINGS

FIG. 1 is a block diagram showing the formation of an endoscope system.

FIG. 2 is a circuit diagram showing the formation of a photometric circuit.

FIGS. 4 and 5 relate to the second embodiment of the present invention.

FIG. 4 is a circuit diagram showing the formation of a photometric circuit.

FIG. 6 is a circuit diagram showing the formation of a photometric circuit.

FIGS. 7(A) to (C) are explanatory diagrams showing the operation of a photometric circuit.

FIG. 8 is a block diagram showing an example of the formation of an electronic endoscope apparatus using an externally fitted television camera for endoscopes.

FIG. 9 is an explanatory view of an endoscope displaying picture by the apparatus in FIG. 8.

FIG. 10 is a waveform diagram showing an image signal on the displaying picture in FIG. 9.

FIG. 11 is a block diagram showing the formation of an electronic endoscope apparatus of this embodiment.

FIGS. 12(A) and (B) are explanatory diagrams for explaining the control of the photometric circuit in the apparatus in FIG. 11.

FIG. 13 is a circuit diagram showing the formation of the photometric circuit in the apparatus in FIG. 11.

DETAILED DESCRIPTION OF THE PREFERRED EMBODIMENTS

Figure 1:
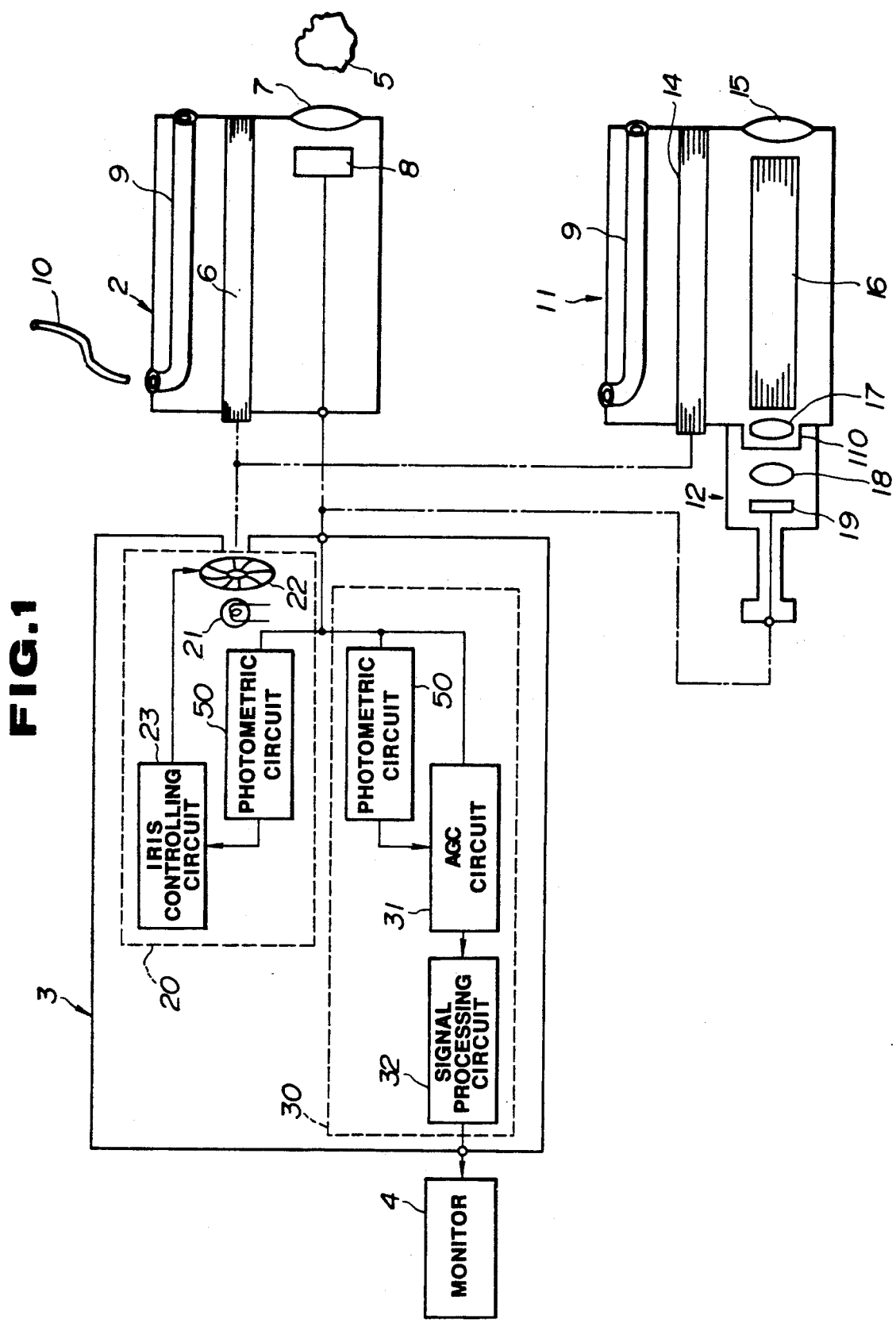
FIGS. 1 to 3 relate to the first embodiment of the present invention.
Figure 2:
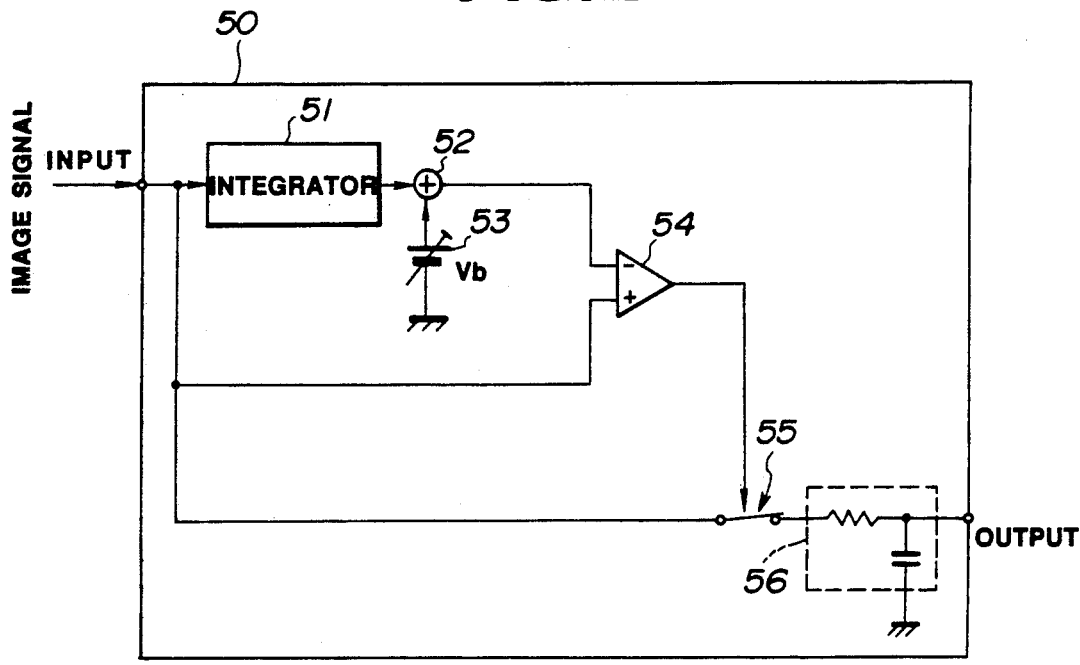
Figure 3A:
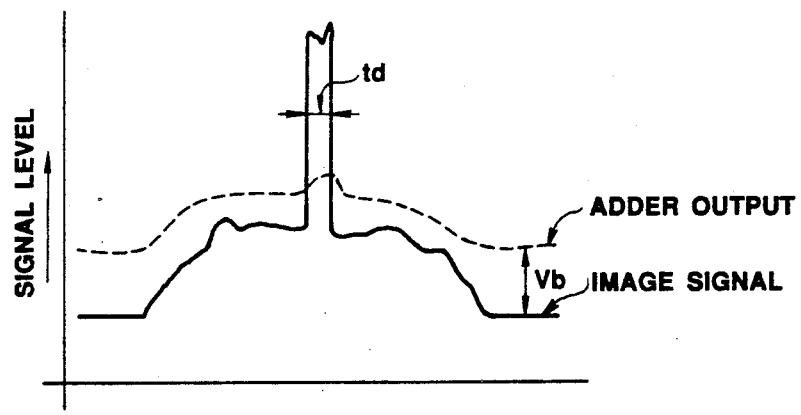
FIGS. 3(A) and (B) are explanatory diagrams showing the operation of a photometric circuit.

FIGS. 1 to 3 show the first embodiment of the present invention.

As shown in FIG. 1, an endoscope system is provided with one of the endoscopes such as an electronic scope 2 or fiber scope 11. The above mentioned fiber scope 11 has an eyepiece part 110 which is to be connected with an endoscope externally fitted television camera (mentioned as a TV camera hereinafter) 12. The above mentioned electronic scope 2 is to be connected to a body unit 3 having a light source part 20 and image signal processing part 30 built-in. The above mentioned fiber scope 11 and TV camera 12 are to be connected to the above mentioned body unit 3. The output signal of the above mentioned body unit 3 is transmitted to a monitor 4 in which an object such as a body cavity interior part 5 is to be displayed.

Each of the above mentioned electronic scope 2 and fiber scope 11 has an insertable part formed to be elongate so as to be insertable into a body cavity, an operating part connected to this insertable part at the rear end and a universal cord extended from this operating part and connectable to the body unit 3. Light guides 6 and 14 transmitting illuminating light are inserted respectively through the insertable parts, operating parts and universal cords of the above mentioned electronic scope 2 and fiber scope 11 so that the illuminating light fed to these light guides 6 and 14 at the entrance ends from a light source part 20 of the body unit 3 may be transmitted to the exit ends and may be radiated toward the body cavity interior part 5 from the exit ends.

An objective lens 7 is provided at the tip of the insertable part of the electronic scope 2 and an imaging device 8 such as a CCD is arranged in the image forming position of this objective lens 7. A signal line connected to this imaging device 8 is inserted through the insertable part, operating part and universal cord and is to be connected to the image signal processing part 30 of the body unit 3. The reflected light from the body cavity interior part 5 has an image formed by the objective lens 7, enters the imaging device 8 and is photoelectrically converted to be an image signal which comes to the body unit 3.

An objective lens 15 is provided at the tip of the insertable part of the fiber scope 11 and the tip surface of the image guide 16 is positioned in the image forming position of this objective lens. This image guide 16 is inserted through the insertable part and is opposed on the rear end surface to an eyepiece lens 17 within the eyepiece part 110 so that the object image formed by the objective lens 15 may be transmitted to the eyepiece part 110 by the image guide 16 and may be observed from this eyepiece part 110. The TV camera 12 connected to this eyepiece part 110 comprises an image forming lens 18 having the light from the above mentioned eyepiece part 110 form an image and an imaging device 19 such as a CCD arranged in the image forming position of this image forming lens 18. A signal line connected to this imaging device 19 is to be connected to the image signal processing part 30 of the body unit 3 so that the object image may be photoelectrically converted by the imaging device 19 to be an image signal which may be input to the body unit 3.

Each of the above mentioned electronic scope 2 and fiber scope 11 has a channel 9 through which the treating instrument 10 can be inserted into a body cavity. There are many treating instruments 10 which can be used as a treating instrument injecting a coloring agent or image forming agent and a treating instrument taking out a part of tissues within a body cavity. Most of the treating instruments are made of white Teflon and metal.

The above mentioned body unit 3 comprises a light source part 20 illuminating an object to be imaged and an image signal processing part 30 outputting an image signal to a monitor 4. The above mentioned light source part 20 comprises a lamp 21, an iris 22 adjusting the light amount of the illuminating light of the lamp 21, an iris controlling circuit generating a control signal for variably controlling the opening rate of the iris 22 and a photometric circuit 50 measuring the illuminating intensities of the light entering the attached imaging device 8 or 19 from the image signals from the imaging devices 8 or 19 and generating a photometric signal transmitted to the iris controlling circuit 23. The above mentioned image signal processing part 30 comprises an AGC circuit 31 amplifying the image signals from the imaging devices 8 and 19 to proper levels, a photometric circuit 50 measuring the illuminating intensities of the illuminating light entering the imaging devices 8 and 19 based on the above mentioned image signals and generating a photometric signal transmitted to the AGC circuit 31 and a signal processing circuit 32 variously processing the output signals of the above mentioned AGC circuit 31 and outputting them to the monitor 4.

The photometric circuit 50 within the light source part 20 comprises an average photometric circuit and a peak photometric circuit. The above mentioned average photometric circuit is a circuit detecting the average value of the brightness level of the image signal of the entire picture and generating a photometric signal corresponding to the average value so that, in case the average value of the brightness level is high, the opening of the above mentioned iris 22 may be narrowed and the amount of illuminating light radiated toward the body cavity interior part 5 may be reduced. The above mentioned peak photometric circuit is a circuit detecting the maximum value of the brightness level of the image signal and generating a photometric signal corresponding to the maximum value so that, in case the maximum value of the brightness level is high, the opening of the above mentioned iris 22 may be narrowed and the amount of illuminating light radiated toward the body cavity interior part 5 may be reduced. Either one of these average photometric circuit and peak photometric circuit is selected in response to the observed part and observing purpose.

The AGC circuit 31 within the image signal processing part 30 is a circuit amplifying a) a low brightness level which can not be compensated by making the light amount of the illuminating light a maximum by expanding the opening of the above mentioned iris 22 to a maximum and b) a high brightness level which remains high even when the opening of the iris 22 is made a minimum. That is to say, the AGC circuit 31 will make the gain low when the control signal (photometric signal) level from the photometric circuit 50 is high but will make the gain high when the control signal level is low. The photometric circuit 50 in the image signal processing circuit 30 is the same as the photometric circuit 50 within the light source part 20. The photometric circuit 50 transmits the control signal to the AGC circuit 31 also comprises an average photometric circuit and a peak photometric circuit so that either one of them may be selected in response to the observed part and observing purpose.

The above mentioned photometric circuit 50 shall be explained in the following with reference to FIG. 2. The photometric circuit 50 comprises an integrator 51 integrating the image signals from the imaging devices 8 and 19, a bias voltage source 53 generating a bias voltage, an adder 52 adding the output of the above mentioned integrator 51 and the bias potential Vb from the bias current source 53, a comparator 54 comparing the above mentioned image signal and the output of the above mentioned adder 52 with each other and a photometric integrator 56 integrating the above mentioned image signal input through a switch 55 so that the above mentioned switch 55 may be switched on and off by the output of the above mentioned comparator 54.

In this photometric circuit 50, an image signal is fed to the photometric integrator 56 through the switch 55 from the input end, is integrated by a predetermined time constant by this photometric integrator 56 and is output as a control signal of the iris controlling circuit 23 and AGC circuit 31. The above mentioned image signal is added to one of the intergrator 51 and comparator 54 at the input end.

Figure 3B:
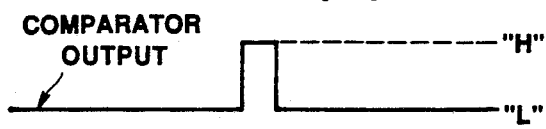

When a treating instrument or the like is used, a bright part having a brightness which is larger than the brightness of the periphery of the image and which is small in spatial size (area) will appear in the image signal. That is to say, as shown by the solid line in FIG. 3(A), the image signal will have a period td in which the signal level is remarkably high. Such an image signal is input into the above mentioned integrator 51, is integrated by a time constant longer than the above mentioned period td and is averaged. The output of this integrator 51 is added to the bias potential Vb of the bias current source 53, set to the minimum value or the like of the image signal level, by the adder 52 and, as shown by the broken line in FIG. 3 (A), the signal level of the image signal becomes an averaged signal level and is applied to one input end of the comparator 54. To the other input end of the comparator is added an image signal which is the same image signal as at the input end of the integrator 51 and has the part with the remarkably high signal level as is shown by the solid line in FIG. 3(A). The output signal of the comparator 54 will be "L" when the image signal is smaller than the output of the adder and will be "H" when the image signal is above the output of the adder. Therefore, as shown in FIG. 3(B), the output of the comparator 54 is usually "L" but will be "H" only in the period td when the image signal level is remarkably high. That is to say, the bright part in the image signal will be extracted. The switch 55 will be on when the output signal of the comparator 54 is "L" but will be off when the output signal is "H".

The time constant of the above mentioned integrator 51 is set in response to the spatial size of the above mentioned bright part to extract only the bright part of a spatial size below a predetermined value. The above mentioned bias potential Vb is set to extract only the bright part of a level difference from the periphery above a predetermined value.

Thus, in the photometric circuit 50 in this embodiment, in the period td when the signal level of the image signal is remarkably high, the image signal will not be applied to the photometric integrator 56 and will be excluded from the photometric object.

Thus, according to the photometric circuit 50 in this embodiment, when the time constant of the integrator 51 and the potential Vb of the bias voltage source 53 are properly selected, the image signal part of the object of a high luminance of the treating instrument or the like used together with the electronic scope 2 or fiber scope 11 will not be applied to the photometric integrator 56, the phenomenon that the entire photographed image becomes dark due to the reduction of the grain of the AGC circuit 31 and the closure of the iris 22 by the iris controlling circuit 23 will be eliminated and the observation of the object will become easy.

Figure 4:
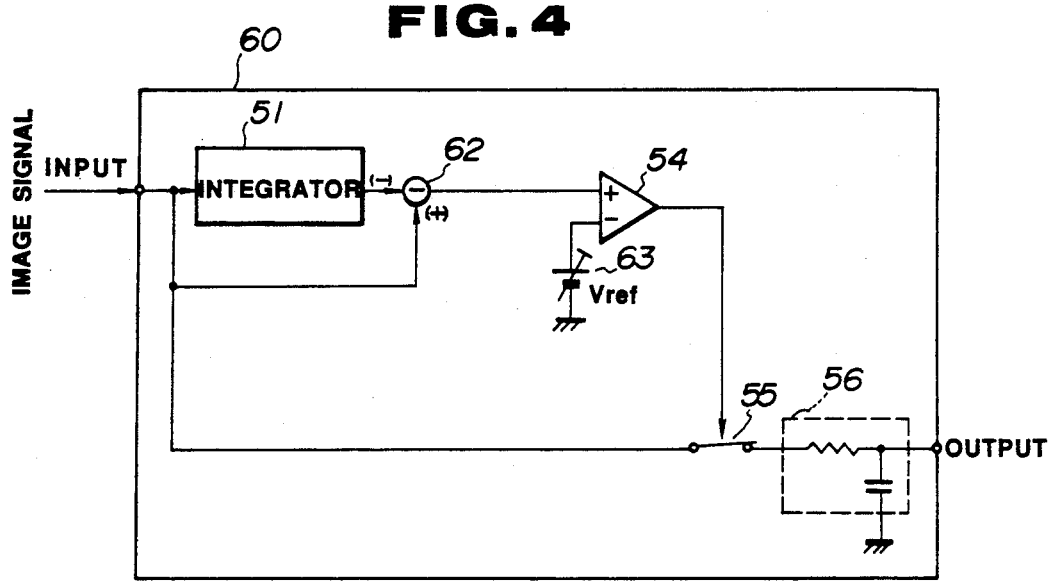

FIGS. 4 and 5 show the second embodiment of the present invention.

The same as in the first embodiment, the photometric circuit 60 shown in FIG. 4 is to be used for the photometric circuits of the light source part 20 and image signal processing part 30 within the body unit 3. This photometric circuit 60 comprises an integrator 51 integrating image signals, a subtractor 62 subtracting the output signal of the above mentioned integrator 51 from the image signal, a reference current source 63 generating a reference potential Vref, a comparator comparing the output signal of the above mentioned subtractor 62 and the reference potential Vref from the above mentioned reference current source 63 with each other, a switch 55 switching the image signal on and off by the output of the comparator 54 and a photometric integrator 56 integrating the image signal input through the switch 55.

In this embodiment, an image signal is fed to the photometric integrator 56 through the switch 55 from the input end of the photometric circuit 60, is integrated by a predetermined time constant by the photometric integrator 56 and is output as a control signal of the AGC circuit 31 and iris controlling circuit 23. The image signal is applied to the input ends of the integrator 51 and subtractor 62.

Figure 5A:
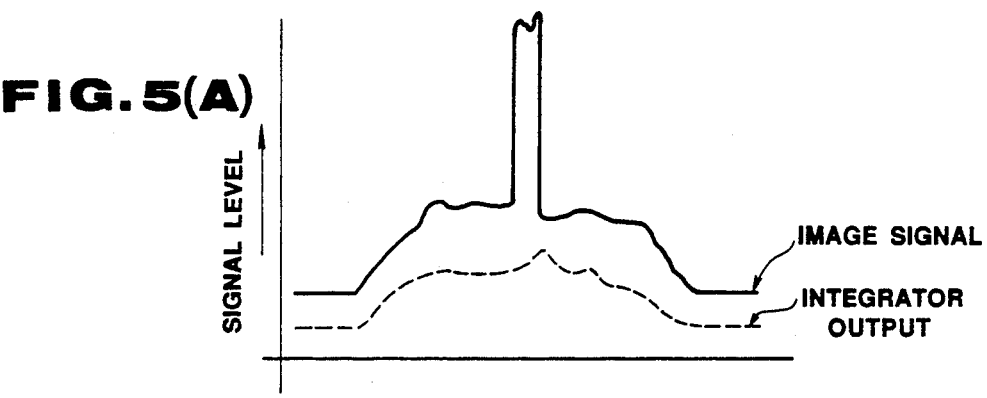
FIGS. 5(A) to (C) are explanatory diagrams showing the operation of a photometric circuit.
Figure 5B:
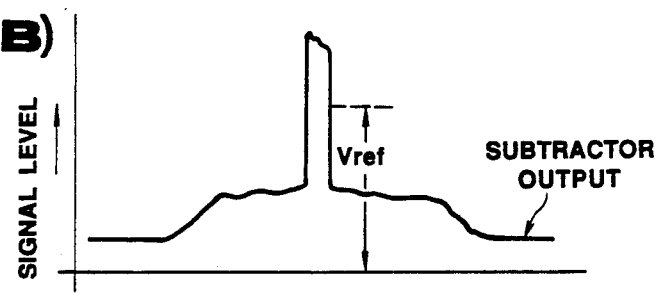
Figure 5C:

An image signal having a period td when the signal level becomes remarkably high as is shown by the solid line in FIG. 5(A) is input into the integrator 51, is integrated by a time constant longer than the above mentioned period td and becomes a signal with an averaged signal level as is shown by the broken line in FIG. 5 (A). The output signal of this integrator 51 is subtracted from the image signal level by the subtractor 62, becomes a signal having a part with a remarkably high signal level of the image signal as shown in FIG. 5(B) and is applied to one input end of the comparator 54. The reference potential Vref of the reference current source 63 is applied to the other input end of the comparator 54. As shown in FIG. 5(C), the output signal of the comparator 54 is usually "L" but will be "H" only in the period when the signal level applied from the subtractor 62 is above the reference potential Vref. The switch 55 will be on when the output signal of the comparator 54 is "L" but will be off when the output signal is "H".

Therefore, in the period td when the signal level of the image signal is remarkably high, the image signal will not be applied to the photometric integrator 56 and will be excluded from the photometric object.

Therefore, even in this embodiment, when the time constant of the integrator 51 and the reference potential Vref of the reference voltage source 63 are properly selected, the same effects as in the first embodiment will be obtained.

The other formations, operations and effects are the same as in the first embodiment.

Figure 6:
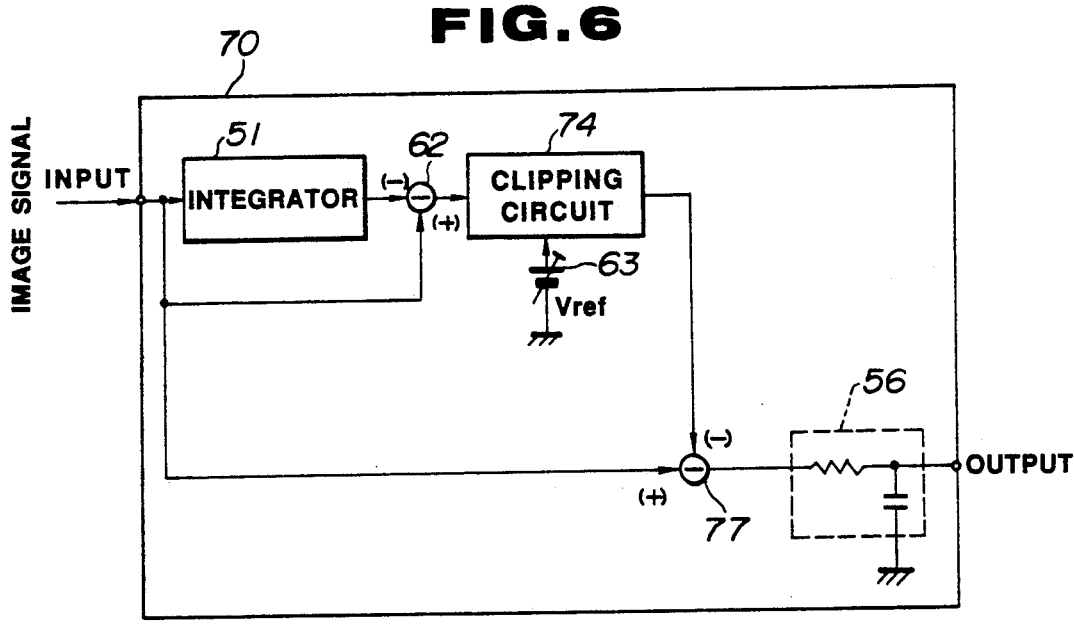
FIGS. 6 and 7 relate to the third embodiment of the present invention.
Figure 7:
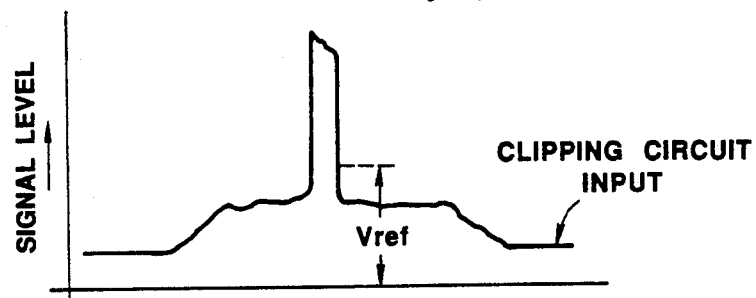
Figure 7:
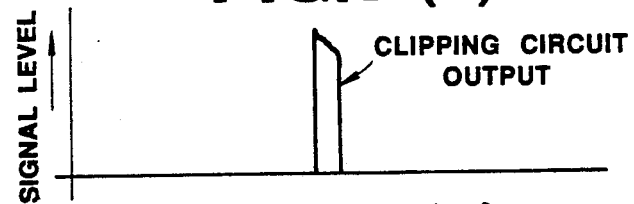
Figure 7:
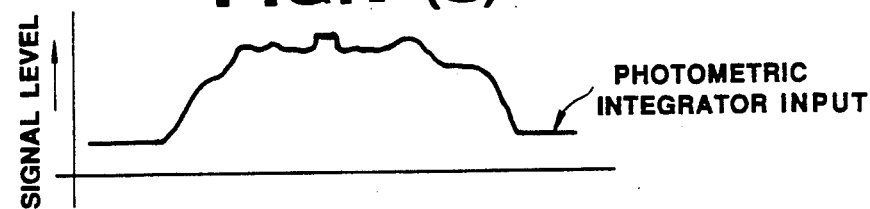

FIGS. 6 and 7 show the third embodiment of the present invention.

The same as in the first embodiment, the photometric circuit 70 shown in FIG. 6 is to be used for the photometric circuits of the light source part 20 and image signal processing part 30 within the body unit 3. This photometric circuit 70 comprises an integrator 51 integrating image signals, a subtractor 62 subtracting the output signal of the above mentioned integrator 51 from the image signal, a reference current source 63 generating a reference potential Vref, a clipping circuit 74 extracting a signal above the reference potential Vref of the above mentioned reference current source 63 among the output signals of the above mentioned subtractor 62, a subtractor 77 subtracting the output signal of the above mentioned clipping circuit 74 from the image signal and a photometric integrator 56 integrating the output of the above mentioned subtractor 77.

In this embodiment, an image signal is applied to the input ends of the integrator 51 and subtractors 62 and 77 from the input end of the photometric circuit 70.

The same as in the second embodiment, an image signal having a period td when the signal level of the image signal becomes remarkably high, as is shown by the solid line in FIG. 5(A), is input into the integrator 51, is integrated by a time constant longer than the above mentioned period td and becomes a signal having an averaged signal level as is shown by the broken line in FIG. 5(A). The output of this integrator 51 is subtracted from the image signal by the subtractor 62, becomes a signal having a part with a remarkably high signal level of the image signal as shown in FIG. 7(A) and is applied to the clipping circuit 74. In this clipping circuit 74, the part of a potential above the clipping potential Vref of the reference current source 63 is extracted and an analogue signal as is shown in FIG. 7(B) is obtained. That is to say, the signal component of the bright part in the image signal is extracted. This signal is subtracted from the image signal by the subtractor 77 and, as shown in FIG. 7(C), an image signal depressed in the part remarkably high in the signal level is obtained. This image signal is applied to the photometric integrator 56, is integrated by a predetermined time constant by the photometric integrator 56 and is output as a control signal of the AGC circuit 31 and iris controlling circuit 23.

In this embodiment, when the time constant of the integrator 51 and the clipping potential Vref of the reference voltage source 63 are properly selected, even in the period td when the signal level of the image signal becomes remarkably high, the same image signal level as in the other period will be able to be applied to the photometric integrator 51 and the photometric integrator 56 will continue the integrating operation.

The other formations, operations and effects are the same as in the first embodiment.

FIGS. 8 to 13 relate to the fourth embodiment of the present invention.

Before explaining the formation of this embodiment, a problem is produced when the area of the image displayed on the monitor for a fiber scope and an externally fitted TV camera, is smaller than the area of the image displayed on the monitor when an electronic scope is used.

Figure 8:
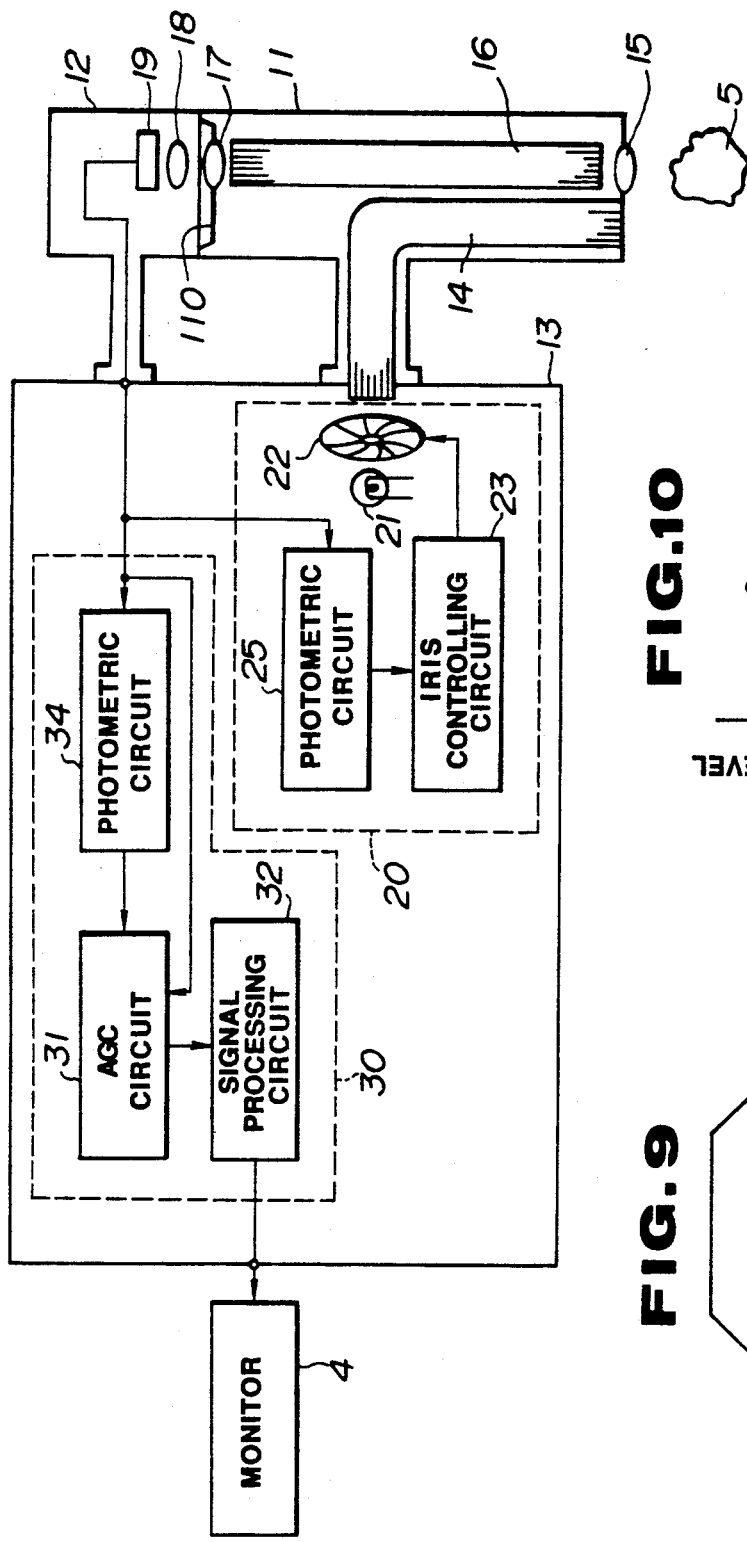
FIGS. 8 to 13 relate to the fourth embodiment of the present invention.

As shown in FIG. 8, an electronic endoscope apparatus using a TV camera comprises an endoscope (fiber scope) 11 using an image guide 16, a TV camera 12 removably connected to an eyepiece part 110 of the above mentioned endoscope 11 and a body unit 13 to which the above mentioned endoscope 11 and TV camera 12 are connected.

The above mentioned endoscope 11 is of the same formation as is shown in FIG. 1 and comprises an insertable part formed to be elongate so as to be insertable, for example, into a body cavity and a thick operating part connected to this insertable part at the rear end. A light guide 14 transmitting an illuminating light is inserted through the insertable part of this endoscope 11 so that the illuminating light fed to the light guide 14 at the entrance end from the body unit 13 may be transmitted to the exit end and may be radiated toward a body cavity interior part 5 from the exit end. The image of the body cavity interior part 5 radiated by this illuminating light is formed at the entrance end of the image guide 16 by an objective lens 15 and may be observed by a naked eye with an eyepiece lens 17 of the eyepiece part 110 provided at the rear end of the above mentioned operating part. The above mentioned TV camera 12 is to be removably connected to this eyepiece part 110.

This TV camera 12 is provided with an image forming lens 18 in a position opposed to the eyepiece lens 17 of the above mentioned endoscope 11 and with an imaging device 19 which is, for example, a CCD at the rear end of this lens 18. The image of the above described body cavity interior part 5 is formed on the imaging surface of the above mentioned imaging device 19. A signal line is connected to the above mentioned imaging device 19 and is removably connected to the above mentioned body unit 13.

The above mentioned body unit 13 comprises a light source part 20 illuminating an object to be imaged and an image signal processing part 30 outputting an image signal to a monitor 4. The above mentioned light source part 20 comprises a lamp 21, an iris 22 adjusting the light amount of the illuminating light of this lamp 21, an iris controlling circuit 23 generating a control signal for variably controlling the opening rate of this iris 22 and a photometric circuit 25 measuring the illuminating intensity of the light entering the imaging device 19 from the image signal and generating a signal to the iris controlling circuit 23. The above mentioned image signal processing part 30 comprises an AGC circuit 31 amplifying the image signal to be of a proper level, a photometric circuit 34 measuring the illuminating intensity of the illuminating light entering the imaging device 19 from the imaging signal and generating a signal to the AGC circuit 31 and a signal processing circuit 32 variously processing the signal and outputting it to the monitor 4.

Figure 10:
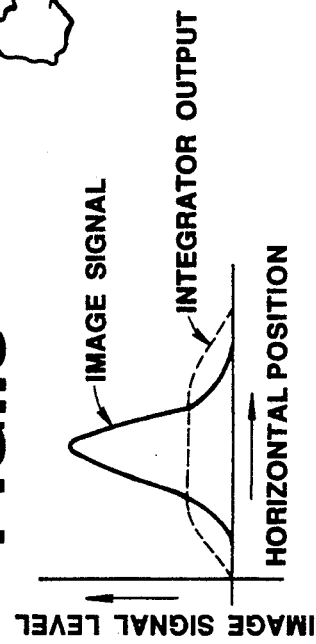
Figure 9:
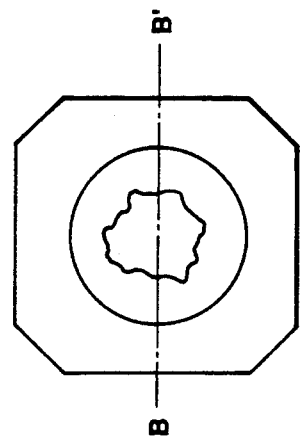

When the above mentioned TV camera 12 is connected to the eyepiece part 110 of the above mentioned endoscope 11 and this endoscope 11 is inserted into a body cavity, the image shown, for example, in the example in FIG. 9 will be able to be observed with the monitor 4. FIG. 10 illustrates in time series the image signal level and the output level of the integrator 51 in the above described embodiment by noting a horizontal scanning line B—B' of the image shown in FIG. 9. As the image observed from the eyepiece part 110 of the endoscope is formed on the imaging device 19 of the TV camera, the area of the image displayed on the monitor 4 will be considerably smaller than the area of the image displayed on the monitor 4 when the electronic scope is used in some case. As shown, for example, in FIG. 10, the image displayed on the monitor 4 is high in luminance, for example, substantially circularly in the same shape as the end surface of the above mentioned image guide 16 with the center part of the picture as a center. Therefore, the image signal level will quickly become high in the center part of the horizontal position as shown by the solid line in FIG. 10 and therefore the output level of the above mentioned integrator 51 will become flat as shown by the broken line in FIG. 10. Therefore, when the photometric circuits shown in the above mentioned respective embodiments are used for the photometric circuits 25 and 34, the greater part of the image signal will not be applied to the above mentioned photometric integrator 56 and the luminance in the center part of the picture will rise to be in a white jumping state. Therefore, in this embodiment, a regulating means for regulating the operation of an input limiting means for limiting the input of the image signal into the photometric circuit is provided to avoid the above described state.

Figure 11:
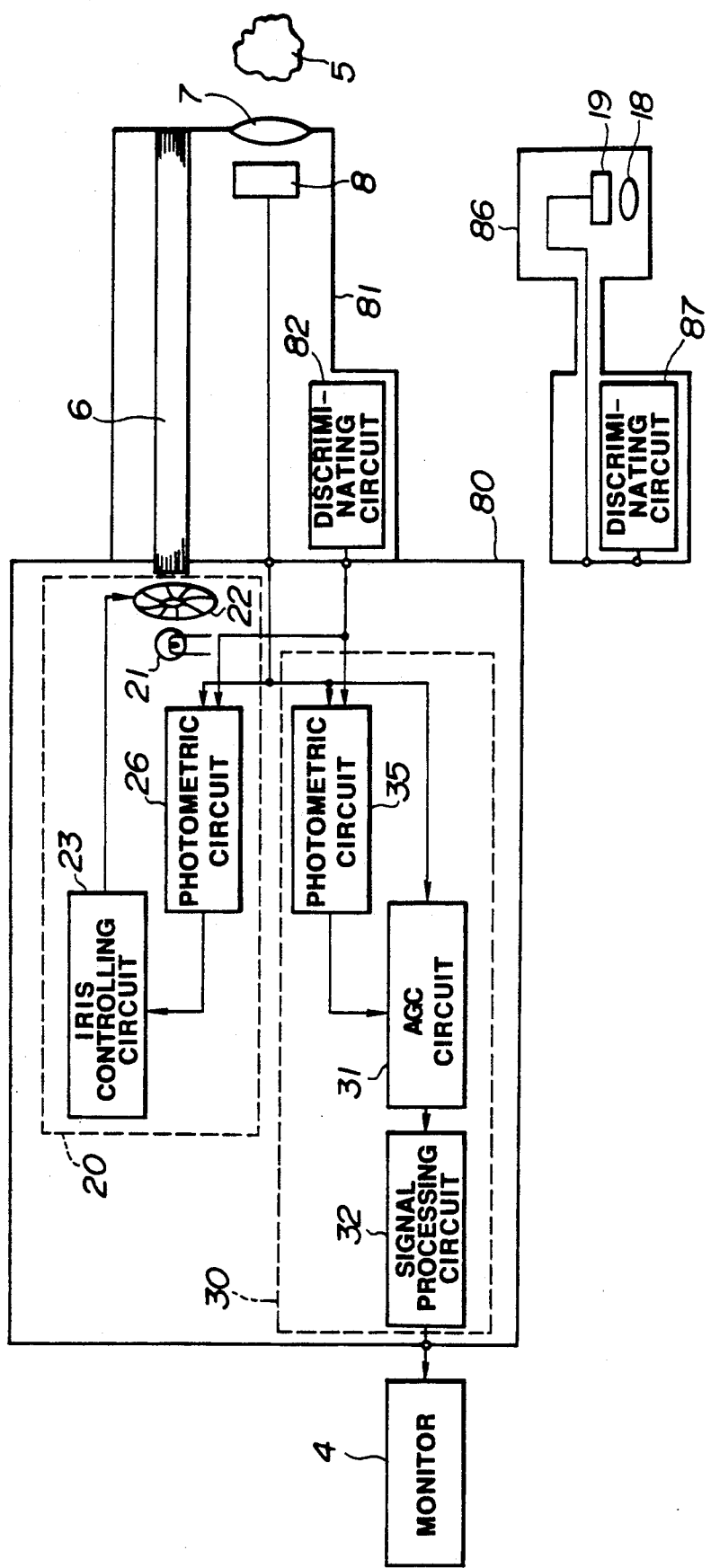
Figure 12:
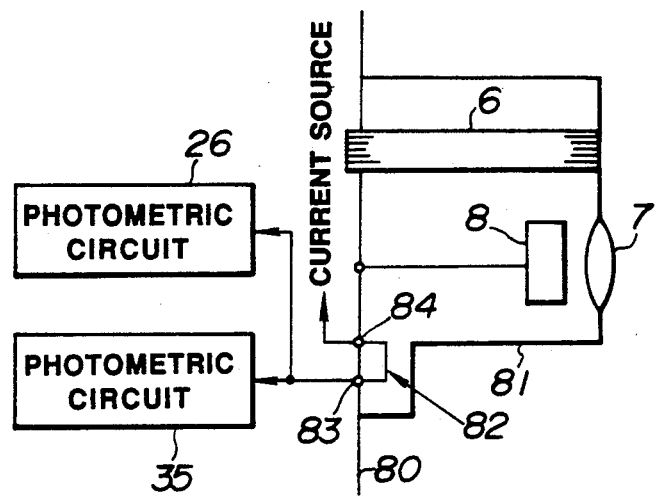
Figure 12:
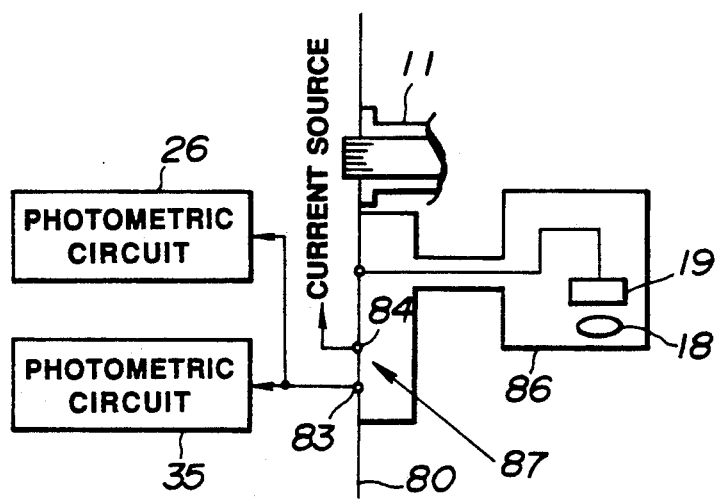

The control means for controlling this regulating means shall be explained by using the electronic endoscope apparatus shown in FIG. 11.

A TV camera 86 connectable to the eyepiece part 110 of an electronic scope 81 or the above mentioned endoscope 11 formed to be elongate so as to be insertable, for example, into a body cavity is to be removably connected to the body unit 80 of the electronic endoscope apparatus. Further, the above mentioned endoscope 11 can be also removably connected.

The light guide 6 transmitting the illuminating light is inserted through the insertable part of the above mentioned electronic scope 81 so that the illuminating light fed to the light guide 6 at the entrance end from the body unit may be transmitted to the exit end and may be radiated toward the body cavity interior part 5 from this exit end. The light reflected from the body cavity interior part 5 is condensed by the objective lens 7, enters the imaging device 8 and is photoelectrically converted to be an image signal which is input to the body unit 80. This electronic scope 81 is provided with a discriminating circuit 82 for controlling the later described photometric circuit.

The above mentioned TV camera 86 is the above described TV camera 12 is provided with a discriminating circuit 87 for controlling the later described photometric circuit.

The above mentioned body unit 80 comprises a light source part 20 feeding an illuminating light to the light guide 14 of the above mentioned endoscope 11 or the light guide 6 of the above mentioned electronic scope 81 and an image signal processing part 30 outputting an image signal to the monitor 4. The above mentioned light source part 20 comprises a lamp 21, an iris 22 regulating the light amount of the illuminating light of this lamp 21, an iris controlling circuit 23 generating a control signal for variably controlling the opening rate of this iris 22 and a photometric circuit 26 measuring the illuminating intensity of the light entering the imaging device 8 of the above mentioned electronic scope 81 or the imaging device 19 of the above mentioned TV camera 86 from the image signal and generating a control signal to the iris controlling circuit 23. The above mentioned image signal processing part 30 comprises an AGC circuit 31 amplifying the image signal, a photometric circuit 35 measuring the illuminating intensity of the illuminating light entering the imaging device 8 of the above mentioned electronic scope 81 or the imaging device 19 of the above mentioned TV camera 86 from the image signal and generating a control signal to the AGC circuit 31 and a signal processing circuit 32 for variously processing the output signal of the above mentioned AGC circuit 31 and outputting the signal to the monitor 4. The discriminating circuit 82 provided in the above mentioned electronic scope 81 or the discriminating circuit 87 provided in the above mentioned TV camera 86 is to be connected to the above mentioned photometric circuits 26 and 35.

As shown, for example, in FIGS. 12(A) and 12(B) the above mentioned body unit 80 is provided with terminals 83 and 84 located between the unit 80 and the above mentioned electronic scope 81 or TV camera 86. The above mentioned terminal 83 is connected to the above mentioned photometric circuits 26 and 35 and the above mentioned terminal 84 is connected to a current source.

As shown, for example, in FIG. 12(A), the above mentioned discriminating circuit 82 is to electrically connect the terminals 83 and 84 with each other within the above mentioned electronic scope 81.

As shown, for example, in FIG. 12(B), the above mentioned discriminating circuit 87 is to leave the terminals 83 and 84 unconnected with each other.

Figure 13:
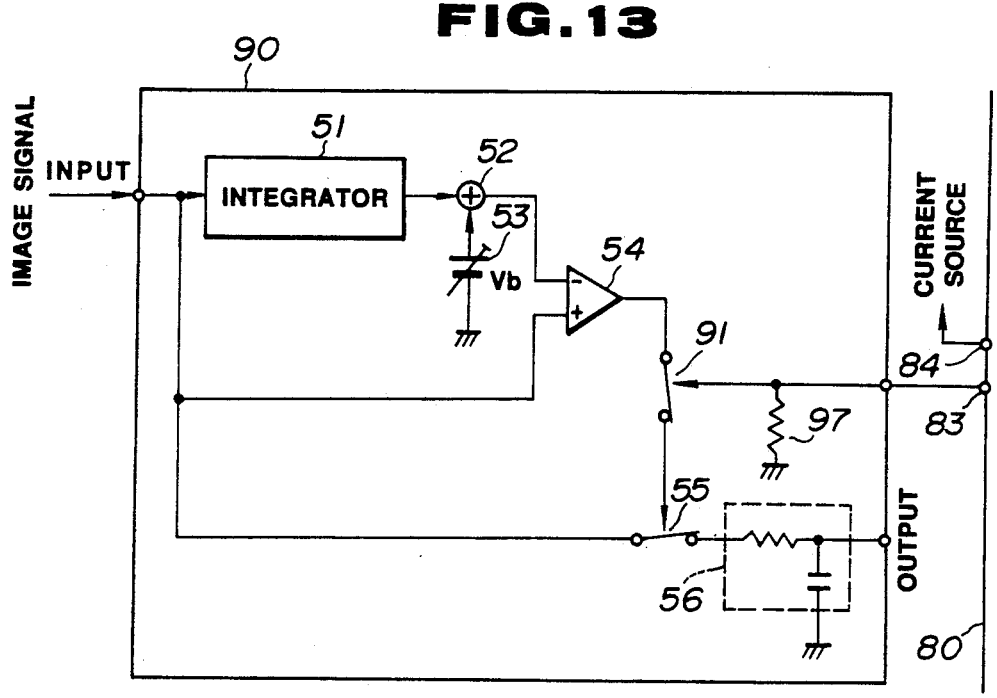

Each of the above mentioned photometric circuits 26 and 35 comprises a photometric circuit 90 shown, for example, in FIG. 13. The components of the same operations as in the above described embodiments shall bear the same reference numerals and shall not be explained here.

The above mentioned photometric circuit 90 comprises an integrator 51, an adder 52, a bias current source 53, a comparator 54, a switch 55, a switch 91 provided between the above mentioned comparator 54 and switch 55 and regulating the above mentioned switch 55 to be controlled by the above mentioned comparator 54, a photometric integrator 56 and a later described resistance 97 to be pulled down. That is to say, this photometric circuit 90 is of the formation of the first embodiment with the addition of the switch 91 and resistance 97.

The control end for switching on and off the above mentioned switch 91 is connected to the above described terminal 83 and is grounded through the above mentioned resistance 97.

The above mentioned switch 91 will be switched on when the current source is fed to the terminal 83, an electric current flows to the resistance 97, a voltage is produced in this resistance 97 and the control end becomes "H". As described above, when the above mentioned electronic scope 81 is connected to the body unit 80, the switch 91 will be on and this photometric circuit 90 will operate the same as in the first embodiment.

The above mentioned switch 91 will be off when the current source is not fed to the terminal 83 and the control end is "L". As described above, when the TV camera 86 is connected to the body unit 80, the switch 91 will be off, the output signal of the above mentioned comparator 54 will not be applied to the switch 55 the switch 55 will be always on and the photometric integrator 56 will continue the integrating operation.

In this embodiment, when it is necessary to observe the low luminance part of a picture, such as when an electronic scope is used, is the same as in the first to third embodiments. Even when it is necessary to observe the high luminance part of a picture, such as when a fiber scope and TV camera are used, a proper photometric operation will be able to be made. The low luminance part and high luminance part can be easily switched over to each other during observation.

The other formations, operations and effects are the same as in the first embodiment.

Figure 14:
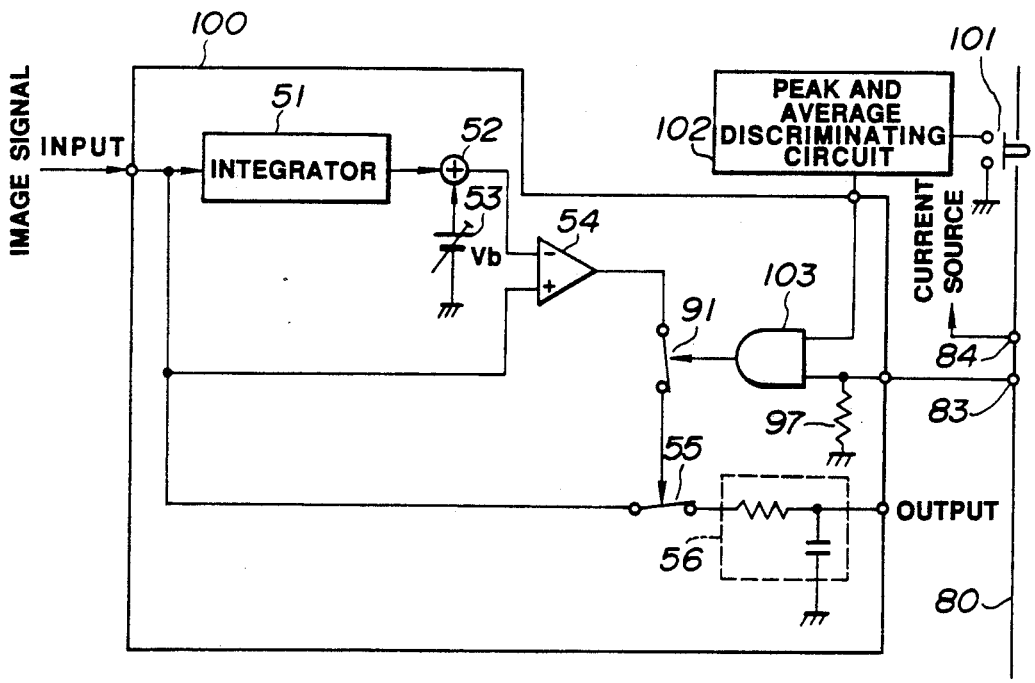
FIG. 14 is a circuit diagram showing the formation of a photometric circuit relating to the fifth embodiment of the present invention.
Figure 15:
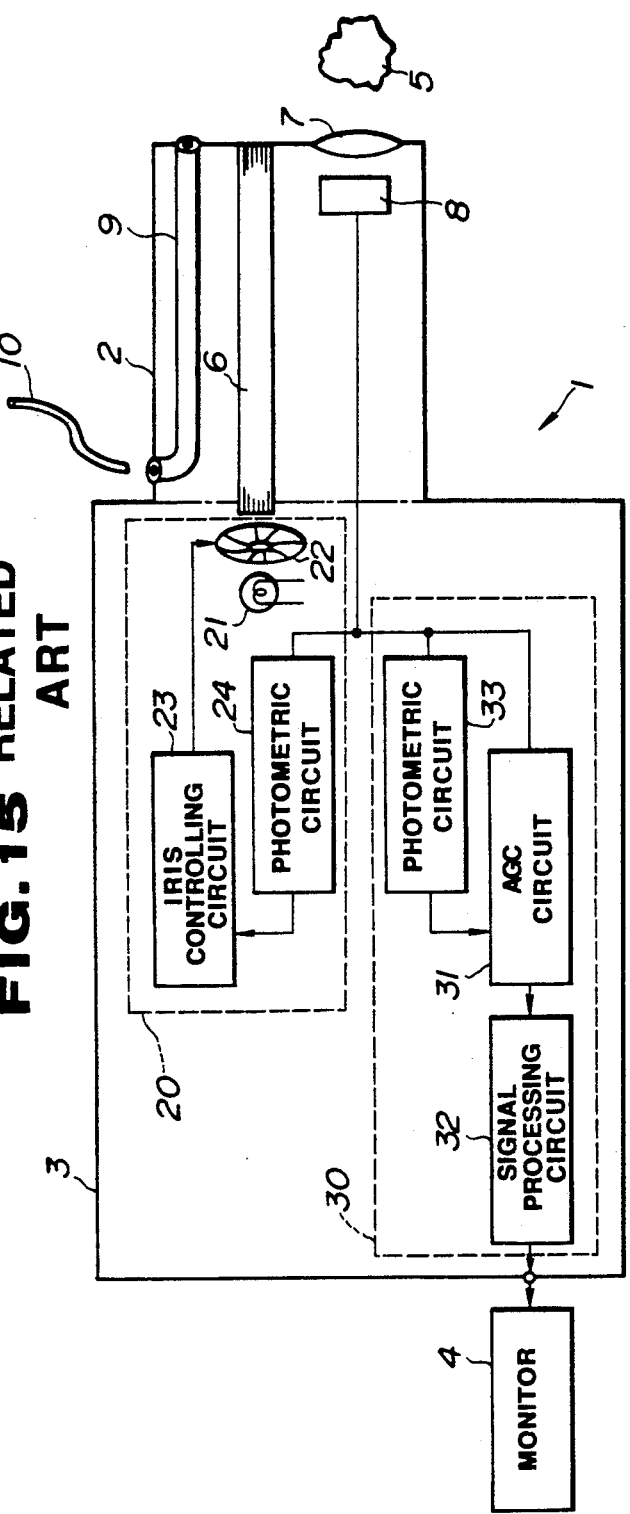
FIG. 15 is a block diagram showing the formation of an electronic endoscope apparatus of a related art example.
Figure 17:
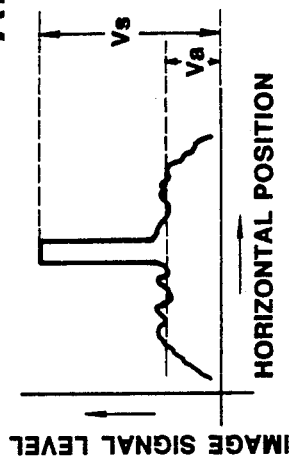
FIG. 17 is a waveform diagram showing an image signal in the displaying picture in FIG. 16.
Figure 16:
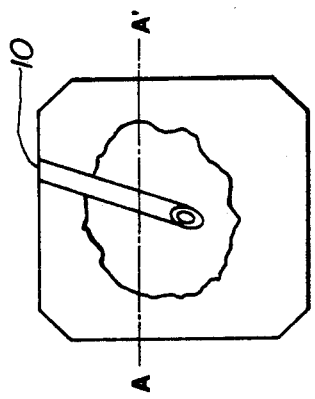
FIG. 16 is an explanatory view showing that a treating instrument appears in an endoscope displaying picture in the apparatus in FIG. 15.

FIG. 14 shows the fifth embodiment of the present invention. The components of the same operations as in the above described embodiments shall bear the same reference numerals and shall not be explained here.

The photometric circuit 100 in this embodiment comprises an integrator 51, an adder 52, a bias current source 53, a comparator 54, a switch 55, a switch 91, a photometric integrator 56, a resistance 97 and an AND circuit 103 controlling the above mentioned switch 91.

The first input end of the AND circuit 103 in the above mentioned photometric circuit 100 is connected to the terminal 83 and is ground through the above mentioned resistance 97. The output end of a later described peak photometry and average photometry discriminating circuit (which shall be mentioned as a peak and average discriminating circuit hereinafter) 102 is connected to the second input end of the above mentioned AND circuit.

A momentary switch (which shall be mentioned as a switch hereinafter) 101 provided, for example, on the outer fitting surface of the above mentioned body unit 80 is connected to the input end of the above mentioned peak and average discriminating circuit 102. When the above mentioned switch 101 is pushed down, the output signal of the output end of the peak and average discriminating circuit 102 will vary alternately to "L" and "H" so as to be "L" during peak photometry and "H" during the average photometry. Whether the photometry is being made by the peak value or average value is displayed, for example, by a displaying part provided in the body unit 80 which is not illustrated.

The control end for switching on and off the above mentioned switch 91 is connected to the output end of the above mentioned AND circuit 103.

The output end of the above mentioned AND circuit 103 will become "H" when the current source is fed to the terminal 83 connected to the first input end, an electric current flows to the resistance 97, a voltage is produced in this resistance 97, the above mentioned first input end becomes "H" and the output signal of the peak and average discriminating circuit 102 connected to the second input end becomes "H". The above mentioned switch 91 will be on when the output end of the above mentioned AND circuit 103 connected to the control end becomes "H". When the above mentioned electronic scope 81 is connected to the body unit and the average photometry is selected, this photometric circuit 90 will operate the same as in the first embodiment.

The output end of the above mentioned AND circuit 103 will be "L" when the current source is not fed to the terminal 83 connected to the first input end and the above mentioned first input end is "L" or the output signal of the peak and average discriminating circuit 102 connected to the second input terminal is "L". The above mentioned switch 91 will be off because the output end of the above mentioned AND circuit 103 connected to the control end is "L". When the TV camera 86 is connected to the body unit 80 or the peak photometry is selected, the output signal of the above mentioned comparator 54 will not be applied to the switch 55, the switch 55 will be always on and the photometric integrator 56 will continue the integrating operation.

Though not illustrated, the photometric integrator 56 will be switched to either of the peak photometric circuit and average photometric circuit in response to the output signal of the above mentioned peak and average discriminating circuit 102.

Thus, according to this embodiment, at the time of average photometry, the same as in the first embodiment, the image signal part of an object of a high luminance such as a treating instrument will not be applied to the photometric integrator 56 and the phenomenon that the entire photographed image becomes dark will be eliminated. At the time of peak photometry, the image signal of a high luminance part will be also applied to the photometric integrator 56 and the iris 22 and AGS circuit 31 will be controlled so that the high luminance part may be of a brightness easy to see.

In this embodiment, there is an effect that, even in the body unit 80 to which the electronic scope is connected, when it is necessary to observe the high luminance part of a picture, the low luminance part and high luminance part will be able to be easily switched over to each other during observation.

In this embodiment, the peak and average discriminating circuit 102 may be provided within the photometric circuit 100.

The output end of the peak and average discriminating circuit 102 may be connected directly to the control end of the switch 91 so that, even when the TV camera 86 is connected, the peak photometry and average photometry may be switched over to each other.

The other formations, operations and effects are the same as in the fourth embodiment.

In case the present invention is used in a photometric circuit of an electronic endoscope apparatus to which an electronic scope is connected, the period td when the image signal level by the treating instrument becomes remarkably high will be 1 to 2 μs in the NTSC television system and, when the time constant of the integrator 51 was set to be about 160 μs, a favorable effect was obtained.

A means for varying the time constant of the integrator 51 in this photometric circuit may be provided in order to obtain the same effects as in the above described embodiments irrespective of the size of the object of a high luminance.

The switch 91 explained in the fourth or fifth embodiment and the formation relating to the switch 91 may be used to control the switch 55 in the second embodiment and the clipping circuit 74 of the subtractor 77 in the third embodiment.

The above described embodiments have been explained by using an electronic endoscope apparatus but may be adapted to any other video camera apparatus.

As described above, according to the present invention, effects that influence an entire photographed picture of an object of a luminance higher than the average luminance of the photographed picture can be easily eliminated and a photographed picture adapted to the situation can be obtained.

The present invention will be effective not only when a treating instrument is used but also in case a halation by the reflection on a mucous membrane of a living body is generated in a medical endoscope or a halation by the reflection on a metal surface is generated in an industrial endoscope.

It is apparent that, in this invention, working modes different in a wide range can be formed on the basis of this invention without deviating from the spirit and scope of the invention. This invention is not restricted by its specific working mode except being limited by the appended claims.

What is claimed is:

1. An endoscope photometric apparatus comprising:
an endoscope imaging apparatus;
a photometric means, connected to said endoscope imaging apparatus, for detecting brightness of an image based on an input image signal from said endoscope imaging apparatus;
an extracting means, connected to said endoscope imaging apparatus, for extracting, from the input image signal from said endoscope imaging apparatus, a bright part of the image signal in which a difference in brightness level at a periphery of the image is above a predetermined value and a spatial size of said bright part is below a predetermined value; and
a limiting means, connected to said endoscope imaging apparatus, said extracting means and said photometric means, for limiting input into said photometric means of a part, corresponding to said bright part, in said image signal by using an output of said extracting means in order to reduce the influence of said bright part on the brightness of the entire image.

2. A photometric apparatus according to claim 1 wherein said extracting means includes an integrating means for integrating said image signal with a predetermined time constant and a means for extracting the part in which a difference between a) the signal integrated by said integrating means and b) said input image signal from said endoscope imaging apparatus, is above a predetermined value.

3. A photometric apparatus according to claim 1 wherein said limiting means includes a means for interrupting the input image signal into said photometric means for the part corresponding to said bright part in said input image signal.

4. A photometric apparatus according to claim 1 wherein said extracting means includes a means for extracting, from said input image signal, a signal component of the bright part which shows a) a range of said bright part and b) the difference in brightness level between said bright part and a periphery of said bright part, and said limiting means includes a depressing means for depressing the part, corresponding to said bright part, in said input image signal in response to the brightness level of the signal component of said bright part.

5. A photometric apparatus according to claim 4 wherein said depressing means includes a means for subtracting the signal component of said bright part from the input image signal before being input into said photometric means.

6. A photometric apparatus according to claim 1 wherein said limiting means has a) an operating state in which limiting operation is performed and b) a non-operating state in which limiting operation is not performed, said photometric apparatus further comprising a selecting means for selecting said operating state and said non-operating state of said limiting means.

7. A photometric apparatus according to claim 6 wherein said selecting means includes a discriminating means for discriminating a type of endoscope imaging apparatus to be connected to said photometric means and for selecting said operating state and said non-operating state in response to a discriminating result of said discriminating means.

8. A photometric apparatus according to claim 7 wherein the types of endoscope imaging apparatuses discriminated by said discriminating means are a) an electronic endoscope including an imaging means and b) a television camera to be connected to an eyepiece part of an endoscope for naked eye observation.

9. A photometric apparatus according to claim 6 wherein said selecting means includes a discriminating means for discriminating different types of photometric systems of said photometric means and for selecting said operating state and said non-operating state in response to a discriminating result of said discriminating means.

10. A photometric apparatus according to claim 9 wherein the photometric systems discriminated by said discriminating means are an average photometric system detecting an average value level of the input image signal and a peak photometric system detecting a maximum value level of the input image signal.

11. An endoscope apparatus comprising:
an endoscope body having an elongate insertable part including an observing window at a tip and an image forming optical system for forming an endoscope image by receiving light, from an object, incident through said observing window;
an imaging means for imaging said endoscope image formed by said imaging forming optical system as an image signal;
a photometric means for detecting brightness of said endoscope image based on the image signal from said imaging means;
a brightness controlling means for controlling the brightness of said endoscope image based on an output of said photometric means;
an extracting means for extracting, from the image signal from said imaging means, a bright part in which a difference in brightness level at a periphery of the endoscope image is above a predetermined value and a spatial size of said bright part is below a predetermined value; and
a limiting means for limiting a part of the image signal input into said photometric means corresponding to said bright part, by using an output of said extracting means in order to reduce the influence of said bright part on the brightness of the entire image.

12. An endoscope apparatus according to claim 11 which further comprises an illuminating means for radiating an illuminating light to said object and wherein said brightness controlling means includes a means for adjusting an amount of illuminating light radiated by said illuminating means.

13. An endoscope apparatus according to claim 11 which further comprises a signal processing means for processing, as a video signal, the image signal from said imaging means and wherein said brightness controlling means includes a means for adjusting the brightness level of said image signal input into said signal processing means from said imaging means.

14. An endoscope apparatus according to claim 11 wherein said imaging means includes an imaging device arranged in an image forming position of said image forming optical system.

15. An endoscope apparatus according to claim 11 wherein said endoscope body further has an eyepiece part provided on a rear end side of said insertable part and an image transmitting means for transmitting to said eyepiece part, said endoscope image formed by said image forming optical system and said imaging means is a television camera to be removably connected to said eyepiece part.

* * * * *

UNITED STATES PATENT AND TRADEMARK OFFICE
CERTIFICATE OF CORRECTION

PATENT NO. : 5,068,719

DATED : November 26, 1991

INVENTOR(S) : Kiyoshi TSUJI et al

It is certified that error appears in the above-identified patent and that said Letters Patent is hereby corrected as shown below:

On the cover page, Item [75], Kiyoshi Tsuji, Musashino, Japan" should read --Kiyoshi Tsuji, Musashino, Japan and Yoshihiro Okada, Hachioji, Japan--.

Signed and Sealed this

Twenty-fifth Day of February, 1992

*Attest:*

HARRY F. MANBECK, JR.

*Attesting Officer*      *Commissioner of Patents and Trademarks*